United States Patent
Liu

(10) Patent No.: US 9,474,305 B2
(45) Date of Patent: Oct. 25, 2016

(54) ELECTRONIC CIGARETTE

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 541 days.

(21) Appl. No.: 14/030,722

(22) Filed: Sep. 18, 2013

(65) Prior Publication Data

US 2015/0034105 A1 Feb. 5, 2015

(30) Foreign Application Priority Data

Aug. 2, 2013 (CN) ..................... 2013 2 0470849 U

(51) Int. Cl.
*A24F 47/00* (2006.01)
*A61M 15/06* (2006.01)

(52) U.S. Cl.
CPC ........... *A24F 47/008* (2013.01); *A24F 47/002* (2013.01); *A61M 15/06* (2013.01)

(58) Field of Classification Search
CPC .... A24F 47/00; A24F 47/002; A24F 47/004; A24F 47/008; A61M 15/06
See application file for complete search history.

(56) References Cited

U.S. PATENT DOCUMENTS

| | | | | |
|---|---|---|---|---|
| 2011/0036346 A1* | 2/2011 | Cohen | ............... | A61M 15/0065 128/200.14 |
| 2013/0160764 A1* | 6/2013 | Liu | ....................... | A61M 15/06 128/202.21 |
| 2014/0109921 A1* | 4/2014 | Chen | ..................... | A24F 47/008 131/273 |
| 2014/0144453 A1* | 5/2014 | Capuano | ............... | A24F 47/008 131/329 |
| 2014/0182612 A1* | 7/2014 | Chen | ..................... | A24F 47/008 131/329 |

FOREIGN PATENT DOCUMENTS

CN WO 2014101734 A1 * 7/2014 ........... A24F 47/008

* cited by examiner

*Primary Examiner* — Anthony Calandra
(74) *Attorney, Agent, or Firm* — Tim Tingkang Xia, Esq.; Locke Lord LLP

(57) ABSTRACT

The present application provides an electronic cigarette comprising an outer sleeve, an atomizing assembly and a battery assembly both mounted inside the outer sleeve, and a bracket disposed between the atomizing assembly and the battery assembly; at least one first through-hole is defined on a side wall of the outer sleeve; the bracket includes a bracket body; a cylindrical first clearance is formed between an outer peripheral surface of the bracket body and an inner surface of the outer sleeve; a channel configured for air flow is formed from the first through-hole through the first clearance to the atomizing assembly. When implementing the present application, the following advantageous effects can be achieved: a cylindrical first clearance is formed between an outer peripheral surface of the bracket body and an inner surface of the outer sleeve, so that the operation for assembling the bracket can be easily achieved.

12 Claims, 2 Drawing Sheets

ELECTRONIC CIGARETTE

CROSS-REFERENCE TO RELATED APPLICATIONS

This non-provisional application claims priorities under 35 U.S.C. §119(a) on Patent Application No. 201320470849.6 filed in P.R. China on Aug. 2, 2013, the entire contents of which are hereby incorporated by reference.

FIELD OF THE INVENTION

The present application relates to the field of daily electrical products, and more particularly relates to an electronic cigarette.

BACKGROUND OF THE INVENTION

As shown in FIG. 1, an electronic cigarette in prior art comprises an outer sleeve 100, an atomizing assembly 200 and a battery assembly 300 both mounted inside the outer sleeve 100, and a bracket 400 disposed between the atomizing assembly 200 and the battery assembly 300. A side wall of the outer sleeve 100 is defined a venting hole 101; and the bracket 400 is defined a venting gap 401; a channel configured for air flow is formed from the venting hole 101 through the venting gap 401 to the atomizing assembly 200. When above-described structures are assembled, the venting hole 101 needs to be aligned exactly with the venting gap 401. An operation by this assembly way is fussy, so that the venting hole 101 is easily jammed by the bracket 400.

SUMMARY OF THE INVENTION

The objective of the present application is to provide an electronic cigarette of which the operation for assembling a bracket can be easily achieved, aiming the defects that the operation for assembling the bracket of the electronic cigarette in prior art is fuzzy and the venting hole are easily jammed.

The technical solutions of the present application for solving the technical problems are as follows:

In one aspect, an electronic cigarette is provided, and the electronic cigarette comprises an outer sleeve, an atomizing assembly and a battery assembly both mounted inside the outer sleeve, and a bracket disposed between the atomizing assembly and the battery assembly; at least one first through-hole is defined on a side wall of the outer sleeve; the bracket includes a bracket body; a cylindrical first clearance is formed between an outer peripheral surface of the bracket body and an inner surface of the outer sleeve; a channel configured for air flow is formed from the first through-hole through the first clearance to the atomizing assembly.

In one embodiment, the atomizing assembly is defined a fourth through-hole configured for air flow; the bracket further includes a second through-hole defined on an outer peripheral surface of the bracket body and communicated with the fourth through-hole.

The bracket body is a cylindrical structure; the bracket further includes a third through-hole defined along an axial direction of the bracket body; the third through-hole is respectively communicated with the second through-hole and the fourth through-hole. The third through-hole is coaxially disposed on the bracket body. Or the third through-hole is coaxially connected to the fourth through-hole. In another embodiment, the bracket further includes a first butting part; the first butting part extends from an outer peripheral surface of the bracket body abutting the battery assembly to an inner surface of the outer sleeve; the first butting part and an inner surface of the outer sleeve abut against each other. A second clearance is formed between the battery assembly and an inner surface of the outer sleeve; the first butting part is a ring structure; the bracket further includes a first venting recess defined on the first butting part and communicated with the second clearance; an opening of the first venting recess is towards an inner surface of the outer sleeve. More than one first venting recess s disposed; the first venting recesses are uniformly arranged on the first butting part.

In another embodiment, the bracket further includes a second butting part; the second butting part extends from an outer peripheral surface of the bracket body abutting the atomizing assembly to an inner surface of the outer sleeve; the second butting part and an inner surface of the outer sleeve abut against each other. A second clearance is formed between the battery assembly and an inner surface of the outer sleeve; the second butting part is a ring structure; the bracket further includes a second venting recess defined on the second butting part and communicated with the second clearance; an opening of the second venting recess is towards an inner surface of the outer sleeve. More than one second venting recess is disposed; the second venting recesses are uniformly arranged on the second butting part.

In another embodiment, the bracket body is defined a wire hole configured for a conductive wire through it; one end of the conductive wire is electrically connected to the atomizing assembly, and the other end of the conductive wire is electrically connected to the battery assembly. The bracket body is made of one material selected from metal, plastics, ceramic and wood material. A projection of the bracket on an axial cross section of the outer sleeve is I-shaped.

When implementing the electronic cigarette of the present application, the following advantageous effects can be achieved: the electronic cigarette adopts a structure that a cylindrical first clearance is formed between an outer peripheral surface of the bracket body and an inner surface of the outer sleeve, so that the operation for assembling the bracket can be easily achieved; furthermore, when the electronic cigarette is assembled, the first through-hole on a side surface of the outer sleeve is not easily jammed by the bracket.

BRIEF DESCRIPTION OF THE DRAWINGS

The present application will be further described with reference to the accompanying drawings and embodiments in the following, in the accompanying drawings.

In the figures.

Figure 1:
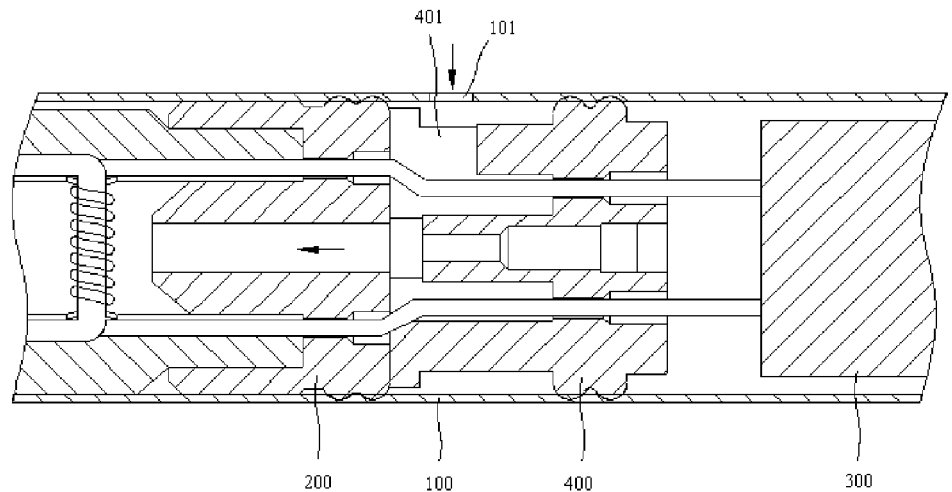
FIG. 1 is a structural schematic view of an electronic cigarette in prior art.

out sleeve 1; first through-hole 11; atomizing assembly 2; fourth through-hole 21; battery assembly 3; bracket 4; bracket body 41; second through-hole 42; third through-hole 43; first butting part 44; second butting part 45; wire hole 46; first venting recess 47; second venting recess 48.

DETAILED DESCRIPTION OF THE PREFERRED EMBODIMENT

To make the technical feature, objective and effect of the present application be understood more clearly, now the specific implementation of the present application is described in detail with reference to the accompanying drawings and embodiments.

Figure 2:
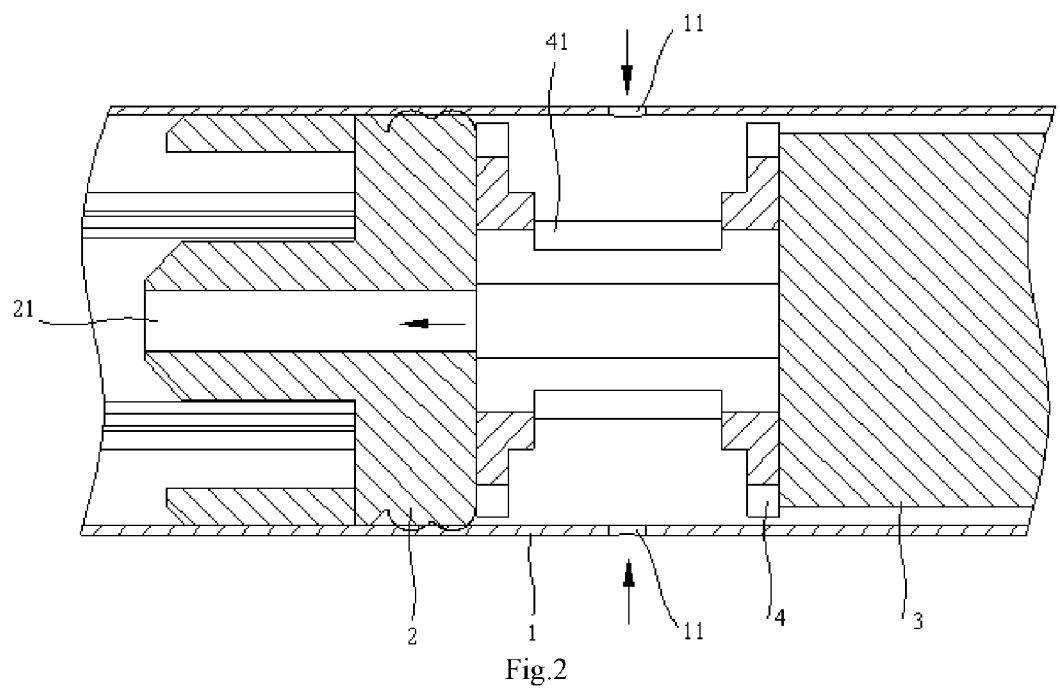
FIG. 2 is a structural schematic view of an electronic cigarette of a preferred embodiment of present application.

As shown in FIG. 2, the present application provides an electronic cigarette; and the electronic cigarette comprises an outer sleeve 1, an atomizing assembly 2, a battery assembly 3 and a bracket 4.

As shown in FIG. 2, the outer sleeve 1 is approximately a hollow cylindrical structure; and a side wall of the outer sleeve 1 is defined at least one first through-hole 11; the first through-hole 11 can be circular or square, etc. . When the atomizing assembly 2 is normally working, air needed mainly enters into the outer sleeve 1 via the first through-hole 11. In this embodiment, two first through-holes 11 are provided, and the two first through-holes 11 are oppositely defined on a side surface of the outer sleeve 1.

As shown in FIG. 2, both the atomizing assembly 2 and the battery assembly 3 are mounted inside the outer sleeve 1. The atomizing assembly 2 is defined a fourth through-hole 21 configured for air flow; and when the atomizing assembly 2 is normally working, air needed enters into the atomizing assembly 2 via the fourth through-hole 21.

A controlling module (not shown) is mounted on a side of the outer sleeve 1. When the electronic cigarette is smoked, the controlling module drives the battery assembly 3 to supply electric power to the atomizing assembly 2, so that the atomizing assembly 2 works to generate smoke. A second clearance is formed between the battery assembly 3 and an inner surface of the outer sleeve 1; and air flow needed during the time when the controlling module is normally working circulates via the second clearance.

Figure 3:
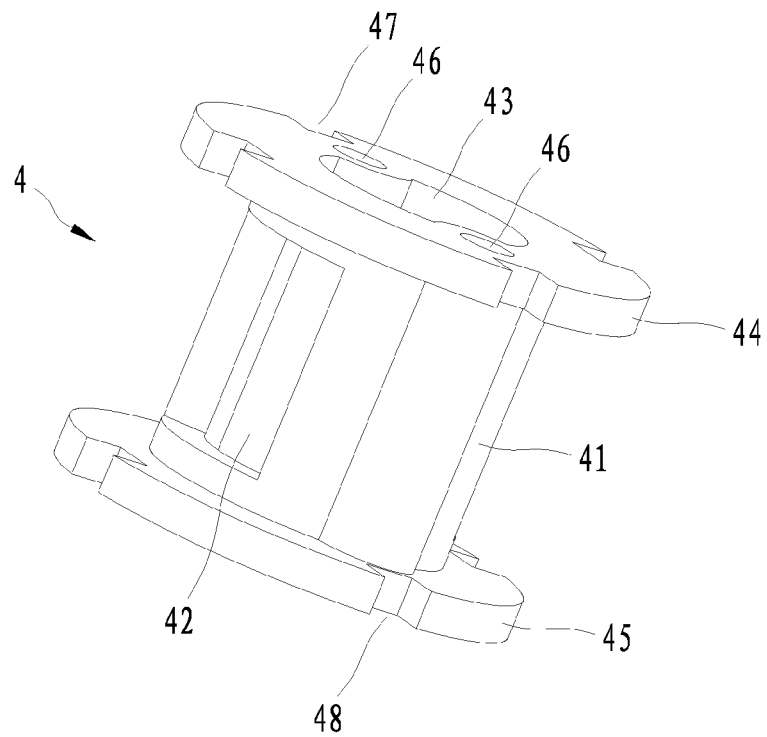
FIG. 3 is a perspective structural schematic view of a bracket of the electronic cigarette shown in FIG. 2.
Figure 4:
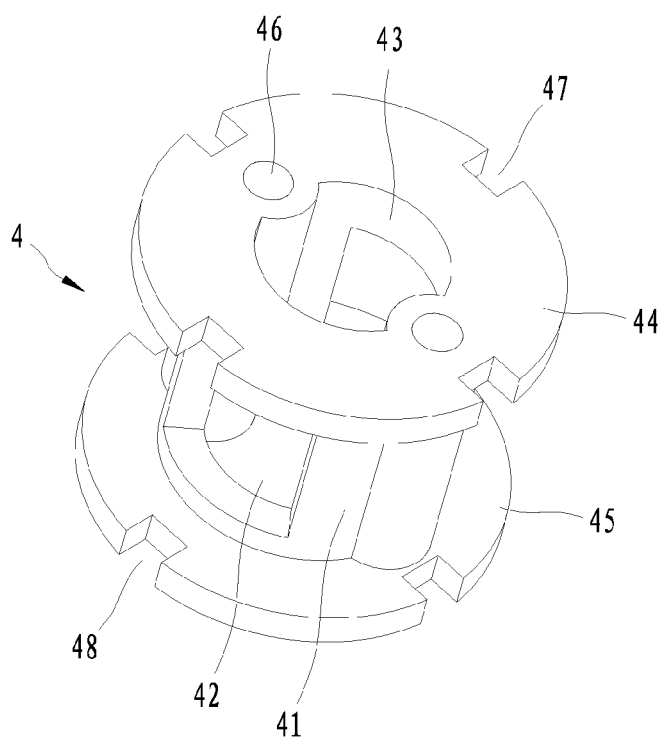
FIG. 4 is another perspective structural schematic view of the bracket shown in FIG. 3.

As shown in FIG. 3, FIG. 4 and FIG. 2, the bracket 4 includes a bracket body 41, a second through-hole 42, a third through-hole 43, a first butting part 44, a second butting part 45, a wire hole 46, a first venting recess 47 and a second venting recess 48. The bracket body 41 is a cylindrical structure; one end of the bracket body 41 abuts against the atomizing assembly 2, and the other end of the bracket body 41 abuts against the battery assembly 3. A cylindrical first clearance is formed between an outer peripheral surface of the bracket body 41 and an inner surface of the outer sleeve 1, namely, the outer diameter of the bracket body 41 is less than the diameter of an inner surface of the outer sleeve 1. A channel configured for air flow is formed from the first through-hole 11 through the first clearance to the atomizing assembly 2. In this embodiment, the bracket body 41 is made of one material selected from metal, plastics, ceramic and wood material, and has high hardness and a certain strength, so that the bracket 4 is not easily deformed in the process of assembly, and has high stability; Furthermore, the bracket 4 has a certain strength, which ensures that the atomizing assembly 2 and the battery assembly 3 are able to be stably mounted inside the outer sleeve 1.

As shown in FIG. 3, FIG. 4 and FIG. 2, the second through-hole 42 is approximately a square structure, and defined on an outer peripheral surface of the bracket body 41. The third through-hole 43 is approximately a circular structure, and defined along an axial direction of the bracket body 41; and the third through-hole 43 is respectively communicated with the second through-hole 42 and the fourth through-hole 21. The third through-hole 43 is coaxially disposed on the bracket body 41, and the third through-hole 43 is coaxially connected to the fourth through-hole 21.

As shown in FIG. 3, FIG. 4 and FIG. 2, the first butting part 44 is a ring structure, and extends from an outer peripheral surface of the bracket body 41 abutting the battery assembly 3 to an inner surface of the outer sleeve 1; the first butting part 44 and an inner surface of the outer sleeve 1 abut against each other, so that the bracket 4 can be firmly mounted inside the outer sleeve 1. The second butting part 45 is also a ring structure; and the second butting part 45 extends from an outer peripheral surface of the bracket body 41 abutting the atomizing assembly 2 to an inner surface of the outer sleeve 1; the second butting part 45 and an inner surface of the outer sleeve 1 abut against each other, so that the bracket 4 can be more firmly mounted inside the outer sleeve 1. In the present embodiment, the bracket body 41, the first butting part 44 and the second butting part 45 are connected to each other and form an I-shaped structure, namely, a projection of the bracket 4 on an axial cross section of the outer sleeve 1 is I-shaped.

As shown in FIG. 3, FIG. 4 and FIG. 2, the wire hole 46 is axially arranged on the bracket body 41, and configured for a conductive wire through it (not shown); one end of the conductive wire is electrically connected to the atomizing assembly 2, and the other end of the conductive wire is electrically connected to the battery assembly 3. In the present embodiment, two wire holes 46 are defined, and the two wire holes 46 are symmetrically defined with respect to the axis of the bracket body 41.

As shown in FIG. 3, FIG. 4 and FIG. 2, the first venting recess 47 is defined on the first butting part 44, and communicated with the second clearance; an opening of the first venting recess 47 is towards an inner surface of the outer sleeve 1. More than one first venting recess 47 is disposed; and the first venting recesses 47 are uniformly arranged on the first butting part 44. In the present embodiment, four first venting recesses 47 are arranged. A second venting recess 48 is defined on the second butting part 45, and communicated with the second clearance; an opening of the second venting recess 48 is towards an inner surface of the outer sleeve 1. More than one second venting recess 48 is disposed; and the second venting recesses 48 are uniformly arranged on the second butting part 45. In the present embodiment, four second venting recesses 48 are also arranged.

As shown in FIG. 2, the process of assembly is as follows: at first, make the bracket 4 respectively abut against the atomizing assembly 2 and the battery assembly 3; and then dispose above-described structures into the outer sleeve 1, and dispose the first through-hole 11 opposite to an outer peripheral surface of the bracket 41. As a first clearance is formed between an outer peripheral surface of the bracket body 41 and an inner surface of the outer sleeve 1, the second through-hole 42 on the bracket 4 doesn't need to be aligned with the first through-hole 11 on the outer sleeve 1, so that the operation for assembling the above-described structures can be easily achieved; when the electronic cigarette is smoked, air needed during the time, when the atomizing assembly 2 is normally working, successively passes through the first through-hole 11, the second through-hole 42, the third through-hole 43 and the fourth through-hole 21 along the arrow direction shown in FIG. 2, so that the atomizing assembly 2 can normally work.

While the embodiments of the present application are described with reference to the accompanying drawings above, the present application is not limited to the above-mentioned specific implementations. In fact, the above-mentioned specific implementations are intended to be exemplary not to be limiting. In the inspiration of the present application, those ordinary skills in the art can also make many modifications without breaking away from the subject of the present application and the protection scope of the claims. All these modifications belong to the protection of the present application.

What is claimed is:

1. An electronic cigarette, comprising an outer sleeve, an atomizing assembly and a battery assembly both mounted inside the outer sleeve, and a bracket disposed between the atomizing assembly and the battery assembly; at least one first through-hole defined on a side wall of the outer sleeve, wherein the bracket includes a bracket body; a cylindrical first clearance is formed between an outer peripheral surface of the bracket body and an inner surface of the outer sleeve; a channel configured for air flow is formed from the first through-hole through the first clearance to the atomizing assembly;

wherein the bracket further includes a first butting part; the first butting part extends from an outer peripheral surface of the bracket body abutting the battery assembly to an inner surface of the outer sleeve; the first butting part and the inner surface of the outer sleeve abut against each other; and wherein a second clearance is formed between the battery assembly and an inner surface of the outer sleeve; the first butting part is a ring structure; the bracket further includes a first venting recess defined on the first butting part and communicated with the second clearance; an opening of the first venting recess is towards an inner surface of the outer sleeve.

2. The electronic cigarette according to claim 1, wherein the atomizing assembly is defined a fourth through-hole configured for air flow; the bracket further includes a second through-hole defined on an outer peripheral surface of the bracket body and communicated with the fourth through-hole.

3. The electronic cigarette according to claim 2, wherein the bracket body is a cylindrical structure; the bracket further includes a third through-hole defined along an axial direction of the bracket body; the third through-hole is respectively communicated with the second through-hole and the fourth through-hole.

4. The electronic cigarette according to claim 3, wherein the third through-hole is coaxially disposed on the bracket body.

5. The electronic cigarette according to claim 3, wherein the third through-hole is coaxially connected to the fourth through-hole.

6. The electronic cigarette according to claim 1, wherein more than one first venting recesses are disposed; the first venting recesses are uniformly arranged on the first butting part.

7. The electronic cigarette according to claim 1, wherein the bracket further includes a second butting part; the second butting part extends from an outer peripheral surface of the bracket body abutting the atomizing assembly to an inner surface of the outer sleeve; the second butting part and the inner surface of the outer sleeve abut against each other.

8. The electronic cigarette according to claim 7, wherein a second clearance is formed between the battery assembly and an inner surface of the outer sleeve; the second butting part is a ring structure; the bracket further includes a second venting recess defined on the second butting part and communicated with the second clearance; an opening of the second venting recess is towards an inner surface of the outer sleeve.

9. The electronic cigarette according to claim 8, wherein more than one second venting recesses are disposed; the second venting recesses are uniformly arranged on the second butting part.

10. The electronic cigarette according to claim 1, wherein the bracket body is defined a wire hole configured for a conductive wire through it; one end of the conductive wire is electrically connected to the atomizing assembly, and the other end of the conductive wire is electrically connected to the battery assembly.

11. The electronic cigarette according to claim 1, wherein the bracket body is made of one material selected from metal, plastics, ceramic and wood material.

12. The electronic cigarette according to claim 1, wherein a projection of the bracket on an axial cross section of the outer sleeve is I-shaped.

* * * * *